(12) United States Patent
Coyne

(10) Patent No.: US 11,766,520 B2
(45) Date of Patent: Sep. 26, 2023

(54) REAGENT-CATALYST DRIVEN SINGLE USE HYDRAULIC DRIVE AND SINGLE USE LARGE VOLUME INJECTOR

(71) Applicant: Nypro Inc., Clinton, MA (US)

(72) Inventor: Joshua Coyne, Clinton, MA (US)

(73) Assignee: Nypro Inc., Clinton, MA (US)

( * ) Notice: Subject to any disclaimer, the term of this patent is extended or adjusted under 35 U.S.C. 154(b) by 262 days.

(21) Appl. No.: 17/207,878

(22) Filed: Mar. 22, 2021

(65) Prior Publication Data

US 2022/0296816 A1 Sep. 22, 2022

(51) Int. Cl.
*A61M 5/315* (2006.01)

(52) U.S. Cl.
CPC ........ *A61M 5/3153* (2013.01); *A61M 5/3159* (2013.01); *A61M 5/31501* (2013.01); *A61M 2205/273* (2013.01)

(58) Field of Classification Search
CPC ............ A61M 5/3135; A61M 5/31501; A61M 5/3159; A61M 5/14244; A61M 5/16877; A61M 5/158; A61M 5/16804; A61M 5/1452; A61M 5/14526; A61M 2005/14204; A61M 2005/1585; A61M 2005/14513
See application file for complete search history.

(56) References Cited

U.S. PATENT DOCUMENTS

2020/0078513 A1* 3/2020 Wei .................. A61M 5/14244

FOREIGN PATENT DOCUMENTS

| KR | 10-2005-0032108 A | 4/2005 |
| KR | 10-2015-0064706 A | 6/2015 |
| KR | 10-2017-0038115 A | 4/2017 |
| KR | 10-2018-0135111 A | 12/2018 |

* cited by examiner

*Primary Examiner* — Rebecca E Eisenberg
*Assistant Examiner* — Justin L Zamory
(74) *Attorney, Agent, or Firm* — Young Basile Hanlon & MacFarlane, P.C.

(57) ABSTRACT

Single use hydraulic drive devices and single use large volume injectors are described. A method for single use hydraulic drive including releasing a holding device to move a catalyst coated portion of a rod into a reagent filled chamber, generating pressure in the chamber due to at least one of gas creation and thermal expansion from a chemical reaction between the catalyst coated portion and the reagent, hydraulically displacing a movable object in hydraulic communication with the chamber, and stopping further chemical reaction when the pressure exceeds a holding device force threshold to enable the holding device to re-hold a retracted catalyst coated portion of the rod outside of the chamber. The self-regulating pressure in the chamber enables a controlled rate of hydraulic displacement of the movable object.

20 Claims, 12 Drawing Sheets

When catalyst is inserted into reagent, gas is produced, driving the plunger.

US 11,766,520 B2

REAGENT-CATALYST DRIVEN SINGLE USE HYDRAULIC DRIVE AND SINGLE USE LARGE VOLUME INJECTOR

TECHNICAL FIELD

This disclosure relates to medical devices and in particular, single use hydraulic drive devices and single use large volume injectors.

BACKGROUND

Single use large-volume injectors (LVIs) are a drug delivery system for the delivery of high-volume drug formulations. For example, LVIs need to deliver or displace a 3 milliliter (ml)-20 ml dose of a high viscosity drug at a controlled rate over a period of time, where a high viscosity drug can include drugs having up to 50 centipoise (CP) and the period of time can be for 5 seconds to 10 minutes, for example. LVIs facilitate safer use of drugs, reduce injection workflow, enable self-administration, and be portable, wearable, and/or disposable.

There are three principle categories of established solutions for the drive mechanism for LVIs including mechanical springs, gas driven, and electromechanical. The mechanical springs are bulky in size and create challenging stresses on surrounding materials during storage. The gas driven devices have environmental concerns, such as being sensitive to temperature. The electro-mechanical devices are costly. In addition, there are other LVI drive mechanisms such as an osmosis pump, hydrogen cells, and expanding battery techniques. The osmosis pump uses osmotic radiant pressure across a semi-permeable membrane to generate pressure. This requires large fluid reservoirs to work. The hydrogen cell produces hydrogen gas through electrolysis to drive injection. In addition to being costly, the hydrogen cell may not be able to generate the higher pressures needed for some LVI applications. The expanding battery or e-cell intentionally causes phenomenon of battery 'puffing' through custom designed Lithium ion batteries. These are limited to 250% expansion size of the battery, making it unsuitable for larger dosages.

Consequently, there is a need for affordably manufacturable and highly compact LVI drive mechanisms.

SUMMARY

Disclosed herein are implementations of single use hydraulic drive devices and single use large volume injectors.

In implementations, a single use large volume injector device including a chamber configured to hold a reagent, a control rod configured for insertion and retraction into the chamber, the control rod including a catalyst coated portion, a holding mechanism configured to maintain the catalyst coated portion external to the chamber, and a syringe in hydraulic communication with the chamber, the syringe configured to hold a defined volume of an injectable fluid which is separated from the reagent by a movable barrier in the syringe. The self-regulating pressure in the chamber enables a controlled rate of injection of the injectable fluid by introduction of the catalyst coated portion into the chamber when the holding mechanism is released, generation of pressure in the chamber due to at least one of gas creation and thermal expansion from a chemical reaction between the catalyst coated portion and the reagent, hydraulic displacement of the movable barrier to inject the injectable fluid at the controlled rate, and retraction of the catalyst coated portion from the chamber when the pressure overcomes the holding mechanism to enable the holding mechanism to hold the catalyst coated portion outside of the chamber.

BRIEF DESCRIPTION OF THE DRAWINGS

The disclosure is best understood from the following detailed description when read in conjunction with the accompanying drawings and are incorporated into and thus constitute a part of this specification. It is emphasized that, according to common practice, the various features of the drawings are not to-scale. On the contrary, the dimensions of the various features are arbitrarily expanded or reduced for clarity.

DETAILED DESCRIPTION

Figure 1:
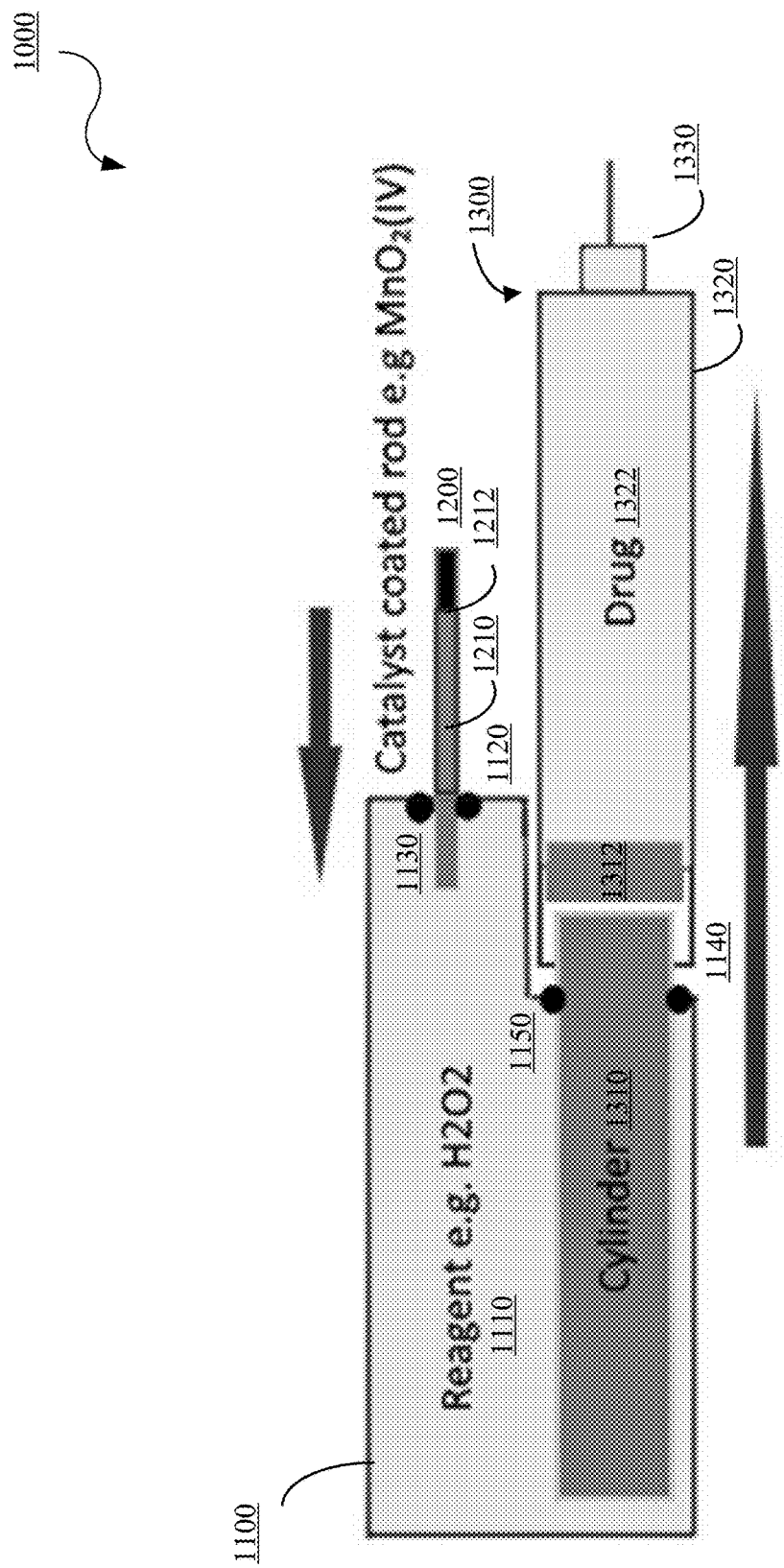
FIG. 1 is a block diagram of an example single use large volume injector in accordance with implementations.

The figures and descriptions provided herein may be simplified to illustrate aspects of the described embodiments that are relevant for a clear understanding of the herein disclosed processes, machines, manufactures, and/or compositions of matter, while eliminating for the purpose of clarity other aspects that may be found in typical similar devices, systems, compositions and methods. Those of ordinary skill may thus recognize that other elements and/or steps may be desirable or necessary to implement the devices, systems, compositions and methods described herein. However, because such elements and steps are well known in the art, and because they do not facilitate a better understanding of the disclosed embodiments, a discussion of such elements and steps may not be provided herein. However, the present disclosure is deemed to inherently include all such elements, variations, and modifications to the described aspects that would be known to those of ordinary skill in the pertinent art in light of the discussion herein.

Embodiments are provided throughout so that this disclosure is sufficiently thorough and fully conveys the scope of the disclosed embodiments to those who are skilled in the art. Numerous specific details are set forth, such as examples of specific aspects, devices, and methods, to provide a thorough understanding of embodiments of the present disclosure. Nevertheless, it will be apparent to those skilled in the art that certain specific disclosed details need not be employed, and that embodiments may be embodied in different forms. As such, the exemplary embodiments set forth should not be construed to limit the scope of the disclosure.

The terminology used herein is for the purpose of describing particular embodiments only and is not intended to be limiting. For example, as used herein, the singular forms "a", "an" and "the" may be intended to include the plural forms as well, unless the context clearly indicates otherwise. The terms "comprises," "comprising," "including," and "having," are inclusive and therefore specify the presence of stated features, steps, operations, elements, and/or components, but do not preclude the presence or addition of one or more other features, steps, operations, elements, components, and/or groups thereof.

The steps, processes, and operations described herein are thus not to be construed as necessarily requiring their respective performance in the particular order discussed or illustrated, unless specifically identified as a preferred or required order of performance It is also to be understood that additional or alternative steps may be employed, in place of or in conjunction with the disclosed aspects.

Yet further, although the terms first, second, third, etc. may be used herein to describe various elements, steps or aspects, these elements, steps or aspects should not be limited by these terms. These terms may be only used to distinguish one element or aspect from another. Thus, terms such as "first," "second," and other numerical terms when used herein do not imply a sequence or order unless clearly indicated by the context. Thus, a first element, step, component, region, layer or section discussed below could be termed a second element, step, component, region, layer or section without departing from the teachings of the disclosure.

As used herein, the terminology "determine" and "identify," or any variations thereof includes selecting, ascertaining, computing, looking up, receiving, determining, establishing, obtaining, or otherwise identifying or determining in any manner whatsoever using one or more of the devices and methods are shown and described herein.

As used herein, the terminology "example," "the embodiment," "implementation," "aspect," "feature," or "element" indicates serving as an example, instance, or illustration. Unless expressly indicated, any example, embodiment, implementation, aspect, feature, or element is independent of each other example, embodiment, implementation, aspect, feature, or element and may be used in combination with any other example, embodiment, implementation, aspect, feature, or element.

As used herein, the terminology "or" is intended to mean an inclusive "or" rather than an exclusive "or." That is unless specified otherwise, or clear from context, "X includes A or B" is intended to indicate any of the natural inclusive permutations. That is if X includes A; X includes B; or X includes both A and B, then "X includes A or B" is satisfied under any of the foregoing instances. In addition, the articles "a" and "an" as used in this application and the appended claims should generally be construed to mean "one or more" unless specified otherwise or clear from the context to be directed to a singular form.

The non-limiting embodiments described herein are with respect to single use hydraulic drive devices and single use large volume injectors. Single use hydraulic drive devices and single use large volume injectors and methods for making the same may be modified for a variety of applications and uses while remaining within the spirit and scope of the claims. The embodiments and variations described herein, and/or shown in the drawings, are presented by way of example only and are not limiting as to the scope and spirit. The descriptions herein may be applicable to all embodiments of the device and the methods for making the devices.

Disclosed herein are implementations of single use hydraulic drive devices and single use large volume injectors and methods for making the single use hydraulic drive devices and single use large volume injectors. The single use hydraulic drive devices and single use large volume injectors use a controlled introduction of a catalyst into a reagent where the resulting chemical reaction produces pressure through either the creation of gasses or through thermal expansion of the reagent, and the pressure is used for hydraulic displacement of an item, object, fluid, or the like. For example, the pressure can be used to displace a liquid drug in a single-use drug delivery device.

A highly compact mechanism is enabled to displace relatively large volumes in a device. The described chemical reactions are capable of manifold increases in volume, and as such, even a relatively small mechanism as described is capable of producing sufficient pressure to displace a large volume of drug. Additionally, the nature of the mechanism is well suited to conforming to external size envelopes due to the flexible nature of hydraulic displacement. For example, the device can be in a folded structure, top-bottom design, and like configurations. These two factors combined have significant advantages in terms of overall size envelope, which is a key factor in the wearable nature of LVIs.

In implementations, a device includes a container for holding pressure which is directly attached to a workpiece such as a prefilled syringe, for example. The container is filled with a reactive reagent, reactant, or the like such as hydrogen peroxide, for example. For example, the catalyst can be Manganese Oxide or Silver if Hydrogen Peroxide is used as the reagent. In implementations, other reactive reagents can be used. In implementations, other reactive reagents can include ammonium dinitramide decomposed by a hexaaluminate catalyst, for example. The device includes a rod which is coated along a portion of the rod with a catalyst suitable for reaction with the reagent. In implementations, the rod can be multiple rods. In implementations, the rod can be helical. In implementations, a surface area of the rod can be sized and shaped in accordance with a defined rate. In implementations, a reagent-reagent chemical reaction can be used to generate the pressure. That is, the rod can be coated with a different reagent then the reagent in the container so long as the reagent coating the rod is not fully consumed prior to completion of the device action. In implementations, other reagent introducing mechanisms can be used in addition to the rod.

The rod is partially inserted through a set of seals in an opening in the container. The rod can be held under pressure by a weak spring or like mechanism so that when the device is activated, the rod is allowed to press further into the container, bringing the catalyst coated surface into contact with the reagent, resulting in a chemical reaction. As the chemical reaction progresses, pressure is generated (through the production of gas and thermal expansion), which drives the prefilled syringe plunger, for example, but also acts against the force of the weak spring holding the catalyst rod in place. If the force increases outside of the desired range it will overcome the force of the weak spring, retracting the catalyst coated surface of the rod, and halting the reaction. In this manner the mechanism self-regulates the reaction and consequently, the rate at which the drug is dispensed. At the end of the syringe plunger's travel the pressure will increase such that the rod is retracted and the reaction halts, completing the delivery. A mechanical lock-out mechanism can be used on the rod to hold it in the retracted position.

In implementations, a variety of mechanisms of converting the pressure of the reaction into mechanical motion can be used to drive the workpiece such as the syringe plunger. In implementations, a device can include mechanisms to isolate a drug, for example, from the temperature of the reaction and the risk of contamination from the reagent. For example, a hydraulic buffer can be used between the reaction container and the syringe plunger. In implementations, the drug can be contained or held in a syringe, a foil pouch, or like container which can be compressed, compacted, or driven via the chemical reaction.

FIG. 1 is a block diagram of an example single use large volume injector device 1000 in accordance with implementations. The single use large volume injector device 1000 can include a container or housing 1100 (collectively "container") which holds or contains a reagent 1110. In implementations, the reagent 1110 can be hydrogen peroxide ($H_2O_2$). The container 1100 includes a rod opening 1120 and a gasket, o-ring, or similar structure 1130 on an inside surface of the container 1100 surrounding or circumscribing the rod opening 1120. The container 1100 includes a drive opening 1140 and a gasket, o-ring, or similar structure 1150 on an inside surface of the container 1100 surrounding or circumscribing the drive opening 1140.

The single use large volume injector device 1000 includes a control rod 1200 configured for insertion and retraction into the container 1100 through the rod opening 1120. The control rod 1200 includes a coated control rod section 1210. In implementations, a surface 1212 of the coated control rod section 1210 is coated, plated, or the like (collectively "coated") with a catalyst. In implementations, the catalyst can be manganese oxide ($MnO_2(IV)$). In implementations, the surface 1212 of the coated control rod section 1210 is coated with a another or different catalyst. As described herein, the control rod 1200 is initially positioned with the coated control rod section 1210 outside or external to the container 1100. In implementations, a variety of mechanical techniques can be used to initially hold the control rod 1200 in position pending activation or triggering of the single use large volume injector device 1000.

The single use large volume injector device 1000 includes a syringe 1300 configured for movable placement in the drive opening 1140. The syringe 1300 includes a piston, plunger, or cylinder 1310, a barrel 1320, and a needle section 1330. The piston 1310 includes a barrier 1312 on one end. The piston 1310 is configured to slide within the barrel 1320. The barrel 1320 is configured to hold a drug 1322.

The single use large volume injector device 1000 is illustrative and may include additional, fewer or different parts, elements, and/or the like which may be similarly or differently architected without departing from the scope of the specification and claims herein. Moreover, the illustrated devices, parts, and/or elements may perform other functions without departing from the scope of the specification and claims herein.

Operationally, activation of the single use large volume injector device 1000 causes the control rod 1200 to ingress or push further into the container 1100, bringing the coated control rod section 1210 into contact with the reagent 1110. The introduction of the coated control rod section 1210 with the reagent 1110 results in a chemical reaction. Pressure is generated due to the production of gas and thermal expansion, which drives the piston 1310 but also acts against the force of the mechanism holding the control rod 1200 in place. If the force due to the pressure increases outside of a desired range, the force from the pressure will overcome the force of the mechanism holding the control rod 1200 in place, retracting the coated control rod section 1210 from the container 1100. This eventually results in halting the chemical reaction. In implementations, a variety of mechanical lock-out techniques can be used to hold the retracted control rod 1200. In implementations, the mechanical techniques for initially holding the control rod 1200, triggering activation of the control rod 1200, and the mechanical lock-out techniques are integrated.

Figure 2A:
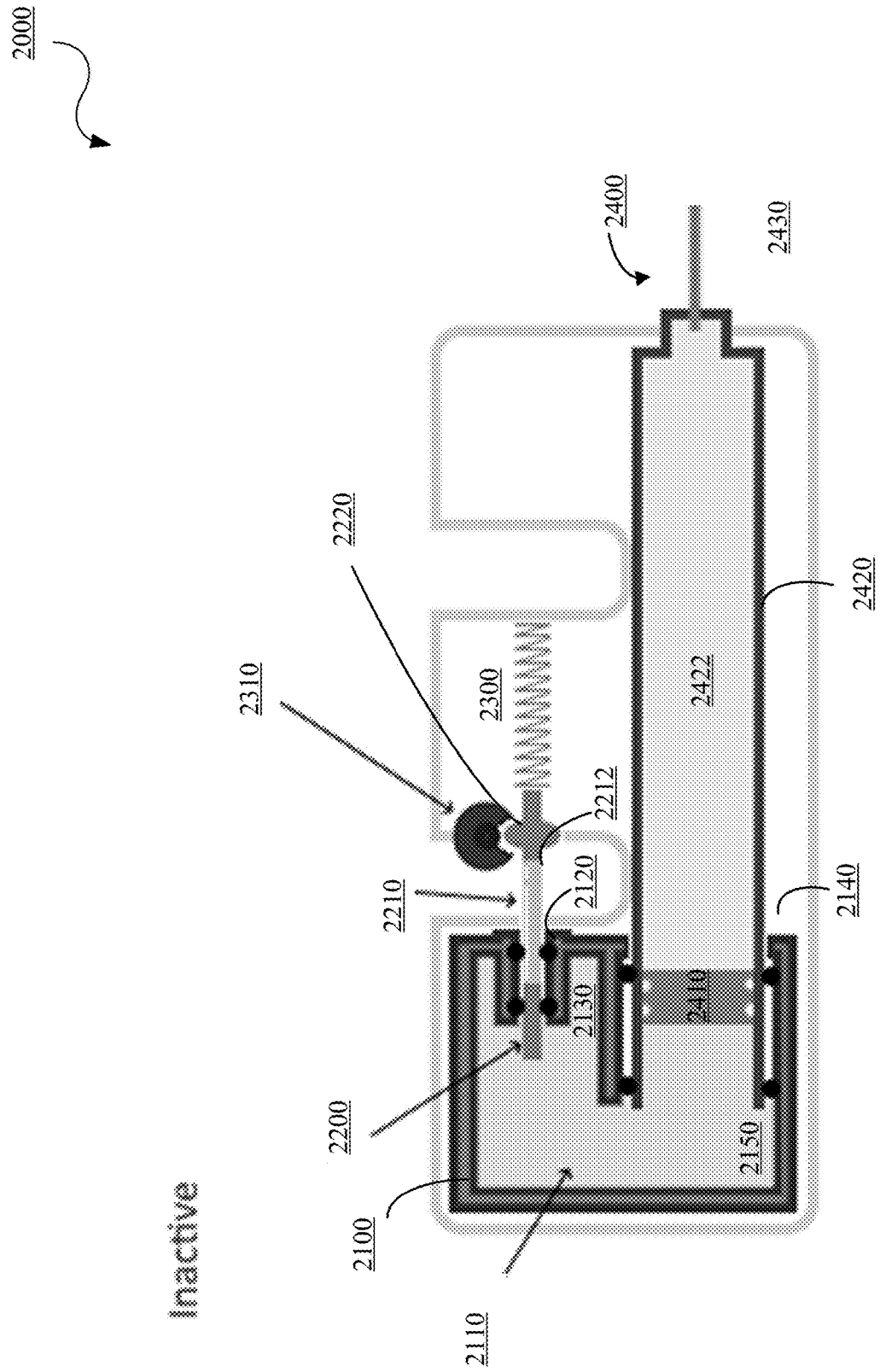
FIG. 2A is a block diagram of an example single use large volume injector in an inactive state in accordance with implementations.
Figure 2B:
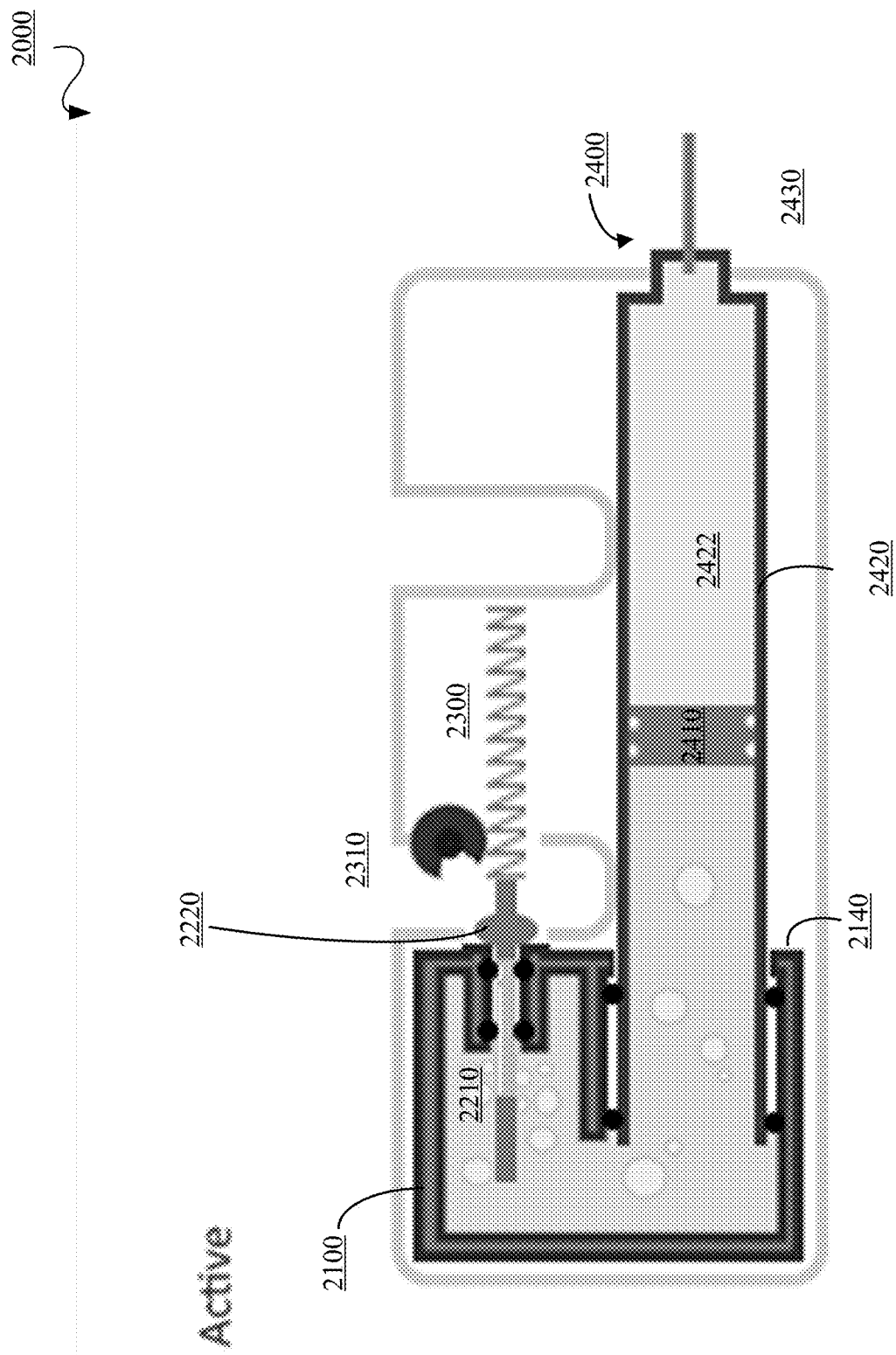
FIG. 2B is a block diagram of an example single use large volume injector in an active state in accordance with implementations.

FIG. 2A is a block diagram of an example single use large volume injector 2000 in an inactive state in accordance with implementations and FIG. 2B is a block diagram of the single use large volume injector 2000 in an active state in accordance with implementations.

The single use large volume injector device 2000 can include a container or housing 2100 (collectively "container") which holds or contains a reagent 2110. In implementations, the reagent 2110 can be hydrogen peroxide ($H_2O_2$). The container 2100 includes a rod opening 2120 and a gasket, o-ring, or similar structure 2130 on an inside surface of the container 2100 surrounding or circumscribing the rod opening 2120. The container 2100 includes a drive opening 2140 and a gasket, o-ring, or similar structure 2150 on an inside surface of the container 2100 surrounding or circumscribing the drive opening 2140.

The single use large volume injector device 2000 includes a control rod 2200 configured for insertion and retraction into the container 2100 through the rod opening 2120. The control rod 2200 includes a coated control rod section 2210. In implementations, a surface 2212 of the coated control rod section 2210 is coated with a catalyst. In implementations, the catalyst can be silver (Ag). In implementations, the surface 2212 of the coated control rod section 2210 is coated with a another or different catalyst. The control rod 2200 includes a retention protuberance, flange, or the like (collectively "protuberance") 2220. In implementations, the retention protuberance 2220 circumscribes the control rod 2200.

As described herein, the control rod 2200 is initially positioned with the coated control rod section 2210 outside or external to the container 2100. The single use large volume injector device 2000 includes a spring 2300 and a release and/or retraction mechanism 2310 which holds the control rod 2200 in position pending activation or triggering of the single use large volume injector device 2000 and when the control rod 2200 retracts from the container 2100 as described herein.

The single use large volume injector device 2000 includes a syringe 2400 configured for placement in the drive opening 2140. The syringe 2400 includes a piston or plunger 2410, a barrel 2420, and a needle section 2430. The barrel 2420 is configured to hold a drug 2422. The piston 2410 is a movable barrier configured to slide within the barrel 2420 and separate the reagent 2110 from the drug 2422.

The single use large volume injector device 2000 is illustrative and may include additional, fewer or different parts, elements, and/or the like which may be similarly or differently architected without departing from the scope of the specification and claims herein. Moreover, the illustrated devices, parts, and/or elements may perform other functions without departing from the scope of the specification and claims herein.

Operationally, in an active state, the spring 2300 and the release and/or retraction mechanism 2310 hold the control rod 2200 in position with the coated control rod section 2210 situated external or outside the container 2100. When the release and/or retraction mechanism 2310 is triggered, the control rod 2200 pushes further into the container 2100 due to the spring 2300, bringing the coated control rod section 2210 into contact with the reagent 2110. The introduction of the coated control rod section 2210 with the reagent 2110 results in a chemical reaction. Pressure is generated due to the production of gas and thermal expansion, which drives the piston 2310 but also acts against the force of the mechanism holding the control rod 2200 in place. If the force due to the pressure increases outside of a desired range, the force from the pressure will overcome the force of the spring 2300, retracting the coated control rod section 2210 from the container 2100. This eventually results in halting the chemical reaction. The release and/or retraction mechanism 2310 holds the control rod 2200 in place.

Figure 3A:
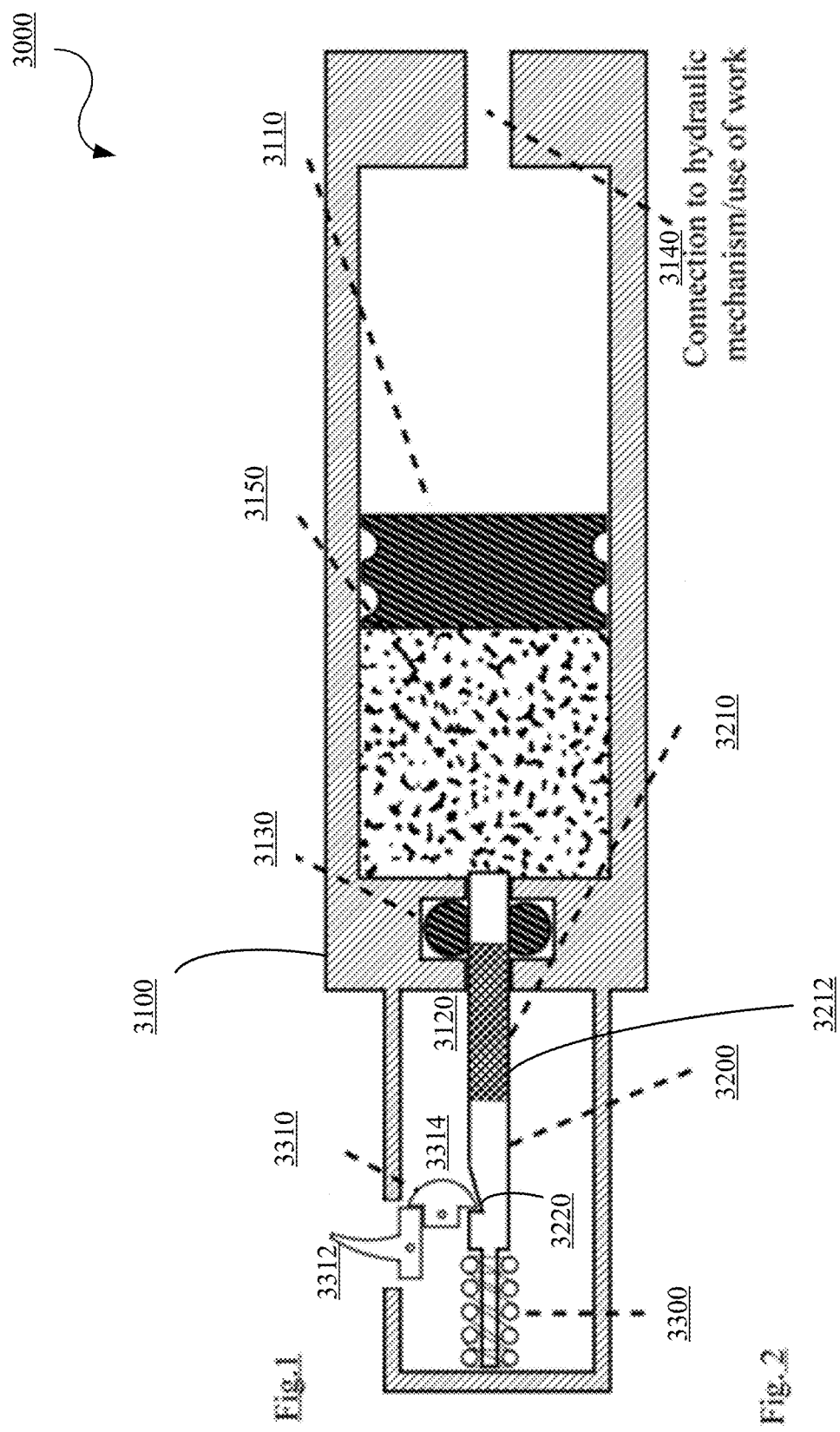
FIG. 3A is a block diagram of an example single use hydraulic drive device in an initial state accordance with implementations.
Figure 3B:
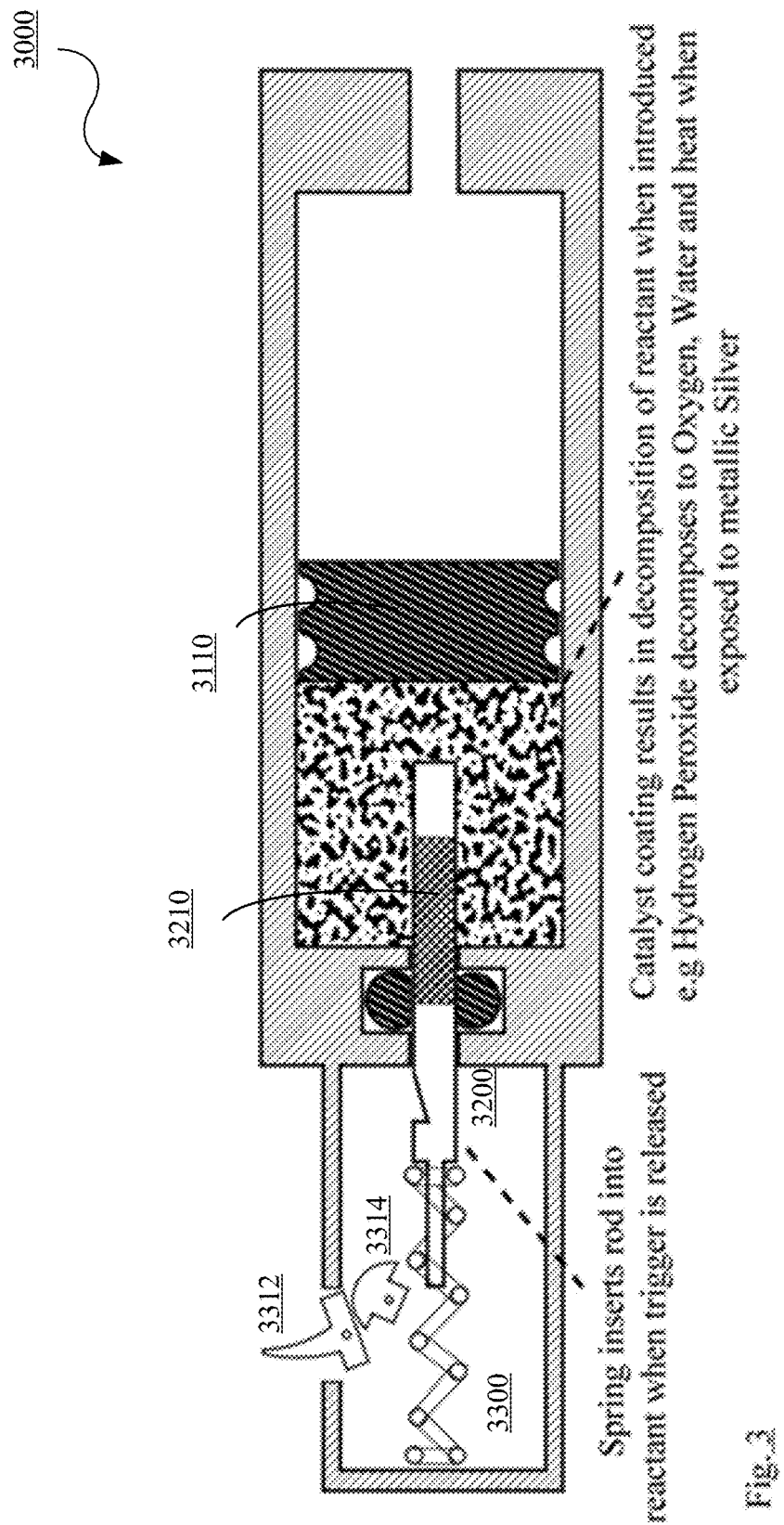
FIG. 3B is a block diagram of an example single use hydraulic drive device in an early transactional state in accordance with implementations.
Figure 3C:
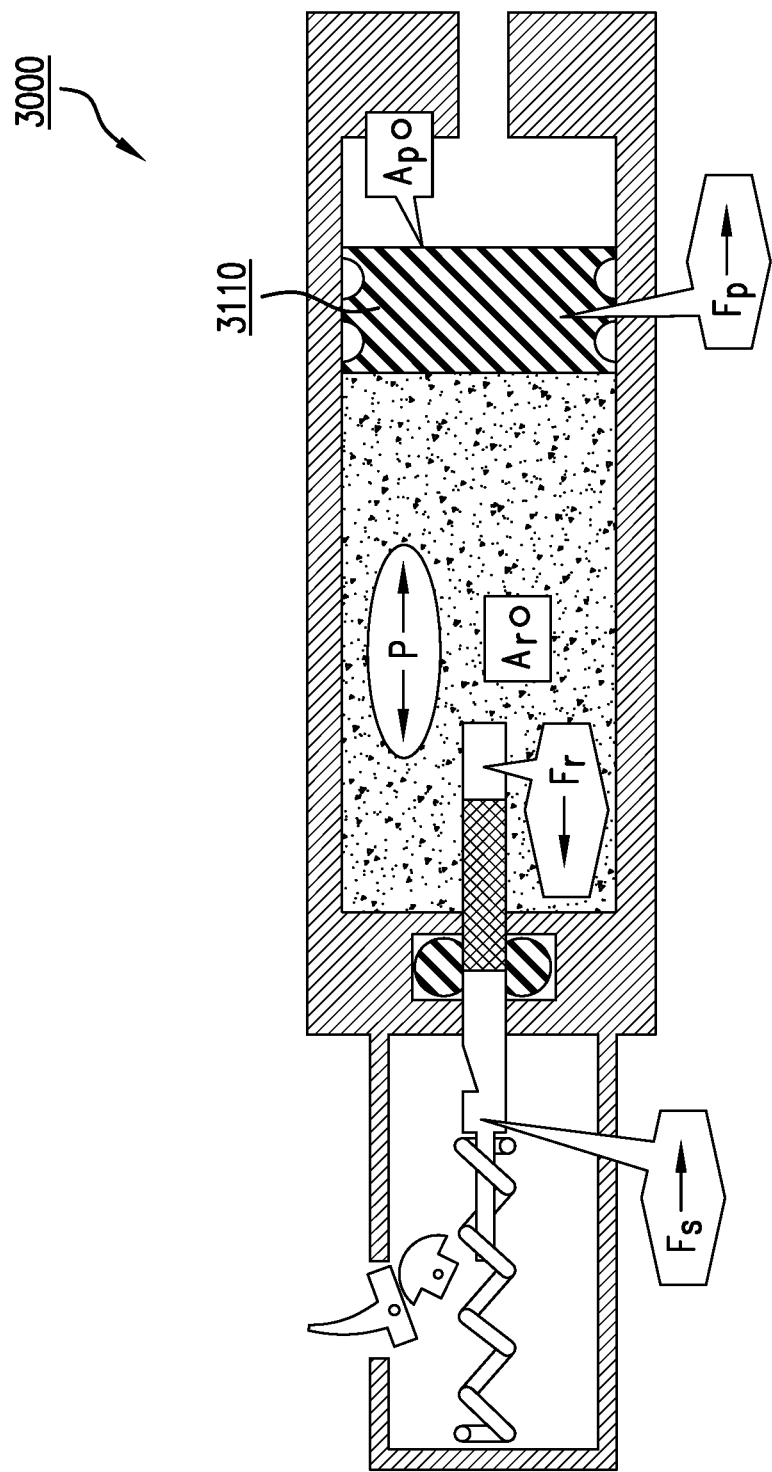
FIG. 3C is a block diagram of an example single use hydraulic drive device in a later transactional state in accordance with implementations.
Figure 3D:
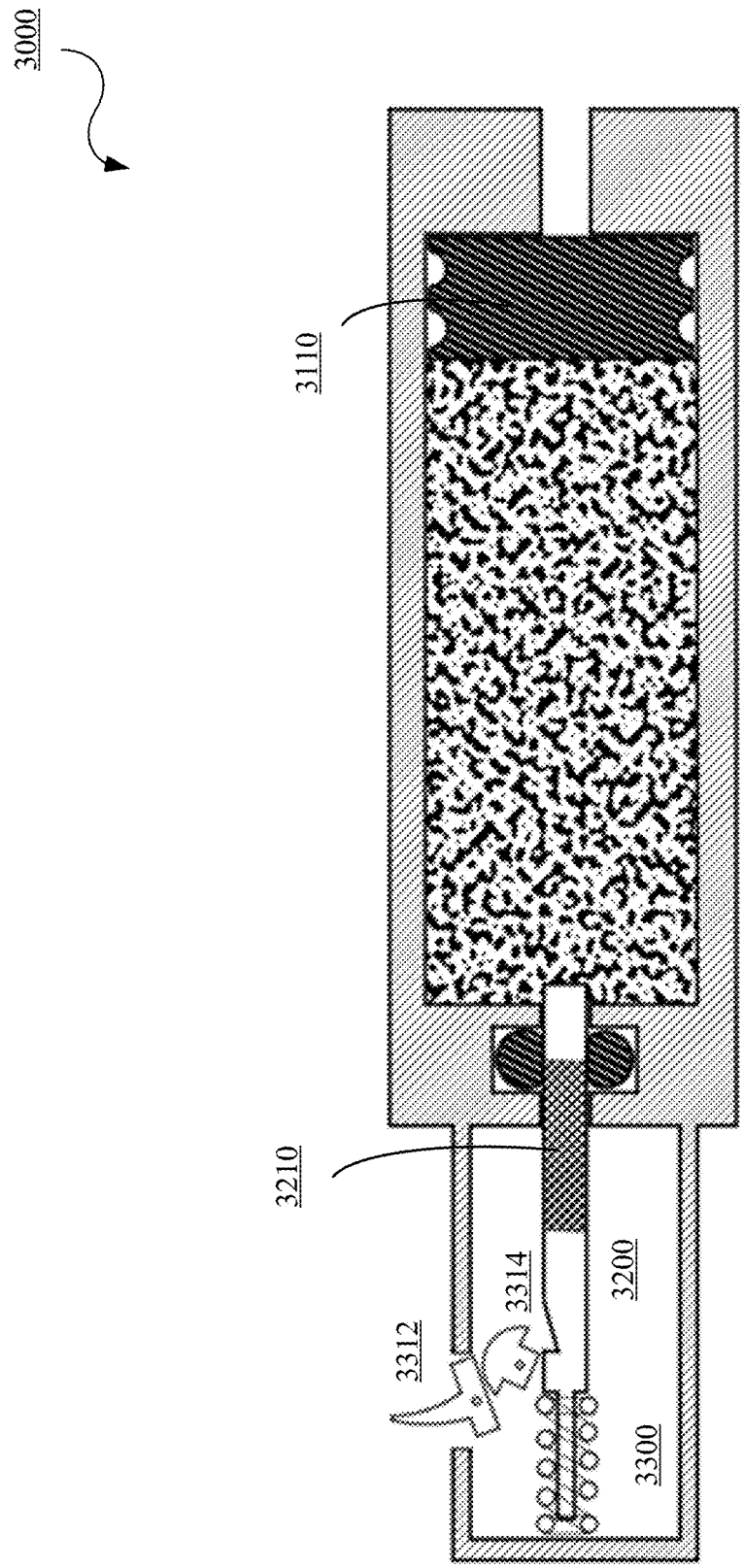
FIG. 3D is a block diagram of an example single use hydraulic drive device in a retracted state in accordance with implementations.

FIG. 3A is a block diagram of an example single use hydraulic drive device 3000 in an initial state accordance with implementations, FIG. 3B is a block diagram of the single use hydraulic drive device 3000 in an early transactional state in accordance with implementations, FIG. 3C is a block diagram of the single use hydraulic drive device 3000 in a later transactional state in accordance with implementations, and FIG. 3D is a block diagram of the single use hydraulic drive device 3000 in a retracted state in accordance with implementations.

The single use hydraulic drive device 3000 can include a container or housing 3100 (collectively "container") with a piston or plunger 3110 which moves within the container 3100. The container 3100 includes a rod opening 3120 and a gasket, o-ring, or similar structure 3130 on an inside surface of the container 3100 surrounding or circumscribing the rod opening 3120. The container 3100 includes a drive opening 3140. In implementations, the drive opening 3140 connects to a hydraulic mechanism, workpiece, and the like. For example, the drive opening 3140 can be connected to a fluid or liquid filled syringe, fluid or liquid filled foil package, and the like. The container 3100 stores, holds, or contains a reagent 3150. In implementations, the reagent 3150 can be hydrogen peroxide ($H_2O_2$).

The single use hydraulic drive device 3000 includes a control rod 3200 configured for insertion and retraction into the container 3100 through the rod opening 3120. The control rod 3200 includes a coated control rod section 3210. In implementations, a surface 3212 of the coated control rod section 3210 is coated with a catalyst. In implementations, the catalyst can be silver (Ag). In implementations, the surface 3212 of the coated control rod section 3210 is coated with a another or different catalyst. The control rod 3200 includes a retention groove, indentation, lip, or the like (collectively "indentation") 3220.

As described herein, the control rod 3200 is initially positioned with the coated control rod section 3210 outside or external to the container 3100. The single use hydraulic drive device 3000 includes a spring 3300 and a trigger mechanism 3310, which includes a trigger 3312 and a release and/or retraction mechanism 3314. The trigger mechanism 3310 holds the control rod 3200 in position pending activation or triggering of the single use hydraulic drive device 3000 and when the control rod 3200 retracts from the container 3100 as described herein.

The single use large volume injector device 3000 is illustrative and may include additional, fewer or different parts, elements, and/or the like which may be similarly or differently architected without departing from the scope of the specification and claims herein. Moreover, the illustrated devices, parts, and/or elements may perform other functions without departing from the scope of the specification and claims herein.

Operationally, in an active state, the spring 3300 is in a compressed state and the trigger mechanism 3310 is engaged with the indentation 3220 to hold the control rod 3200 in position with the coated control rod section 3210 situated external or outside the container 3100. When the trigger 3312 is pulled, switched, or otherwise, the release and/or retraction mechanism 3314 disengages with the indentation 3220 and the control rod 3200 pushes further into the container 3100 due to the spring 3300. The coated control rod section 3210 is brought into contact with the reagent 3150. The introduction of the coated control rod section 3210 with the reagent 3150 results in a chemical reaction. The catalyst coating causes decomposition of the reagent 3150. For example, hydrogen peroxide decomposes into oxygen, water, and heat when exposed to metallic silver. As gas and heat are released by the chemical reaction, pressure [P] rises internally acting on both the control rod 3200 and the piston 3110 until a dynamic equilibrium is reached where any further increase in pressure will cause the axial force on the control rod 3200 [$F_r$] to overcome the spring force [$F_s$] of the spring 3300 and retract the coated control rod section 3210 out of contact with the reagent 3150, halting the reaction. The maximum pressure generated by the reaction [$P_m$] is determined by the force of the spring 3300 and the cross sectional area of the end of the control rod 3200 [$A_r$] (since the remaining pressures on the control rod 3200 balance out). That is, $P_m = F_s/A_r$.

This pressure [$P_m$] acts to create a force on the piston 3110 [$F_p$] which is a function of the cross sectional area of the piston 3110 [$A_p$]. The acting force of the piston 3110 can be determined as a product of the force of the spring 3300 [$F_s$] and the ratio of the areas of the control rod 3200 [$A_r$] and the piston 3110 [$A_p$]. That is, $F_p = F_s(A_p/A_r)$. In addition, given the strong chemical reaction, the effective stroke length of the piston 3110 can be significantly longer than that of the spring 3300. In this fashion, the chemical reaction can be harnessed to do mechanical work substantially greater than the spring 3300 while being regulated by the spring 3300. Once the piston 3110 has reached the end of the travel, i.e., the end of the container 3100, the internal pressure will rise to fully overcome the spring force [$F_s$], fully retracting the control rod 3200 and halting the reaction. The release and/or retraction mechanism 3314 holds the control rod 3200 in place after retraction.

Figure 4A:
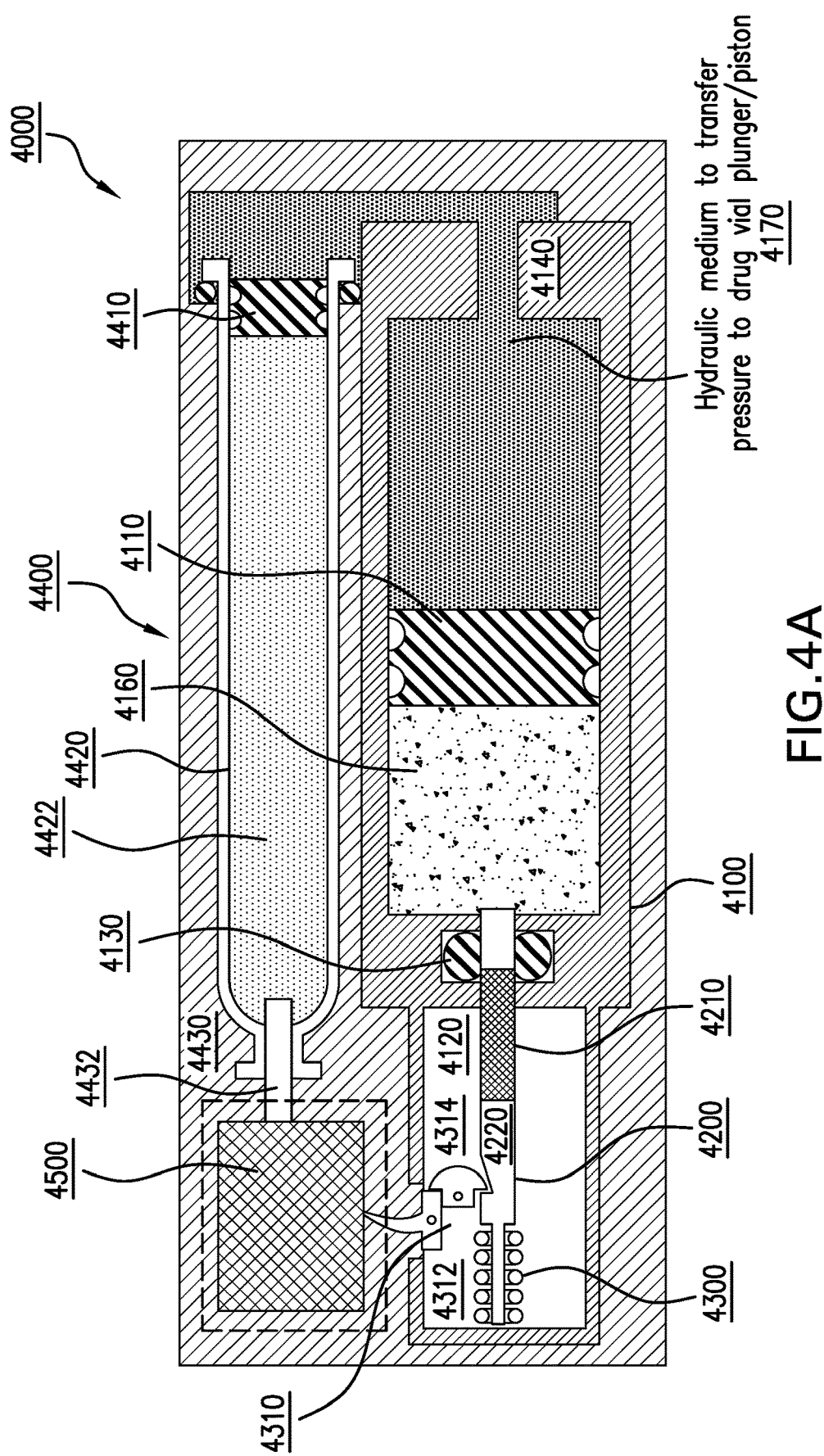
FIG. 4A is a block diagram of an example single use large volume injector in an initial state accordance with implementations.
Figure 4B:
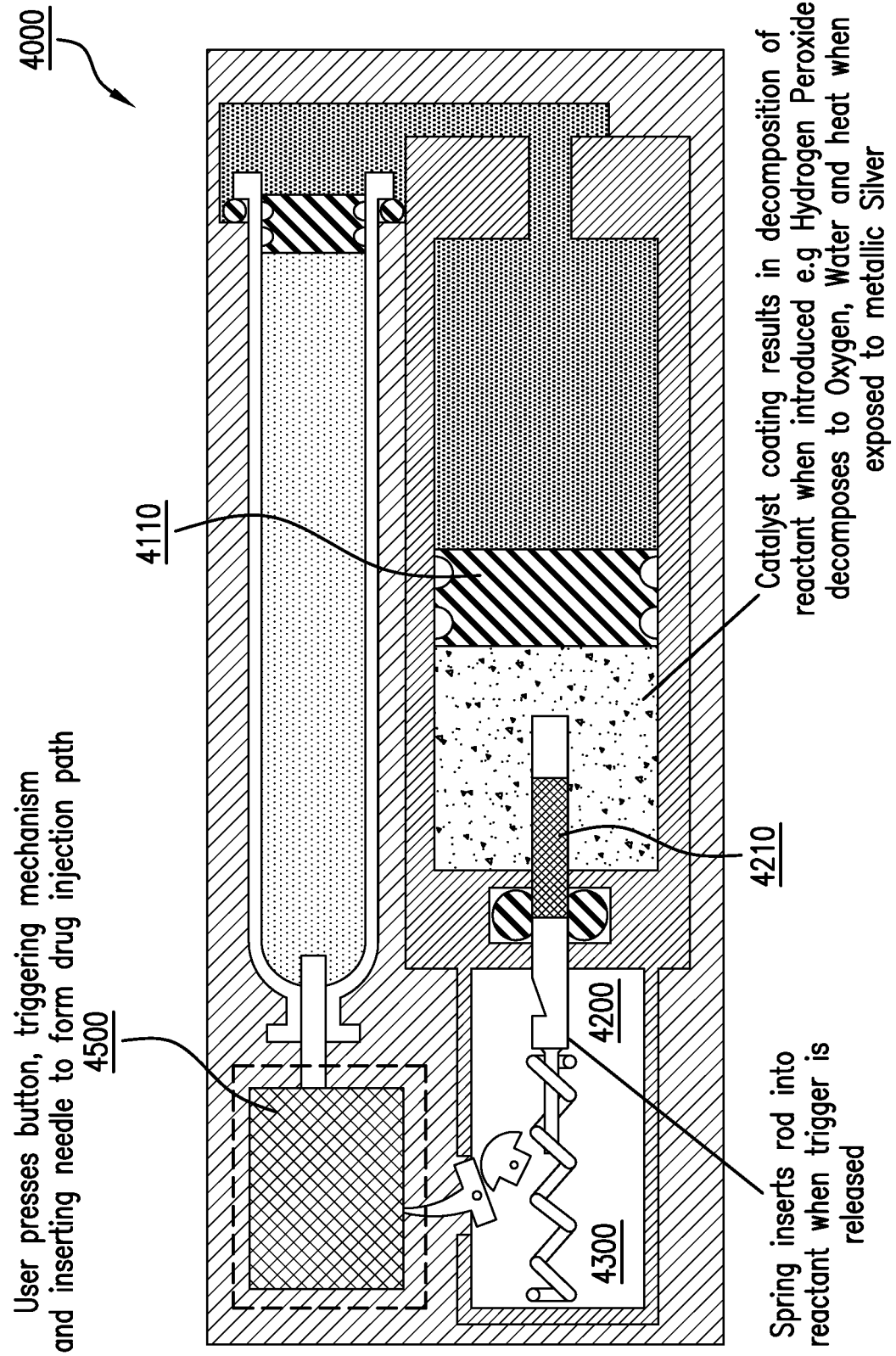
FIG. 4B is a block diagram of an example single use large volume injector in an early transactional state in accordance with implementations.
Figure 4C:
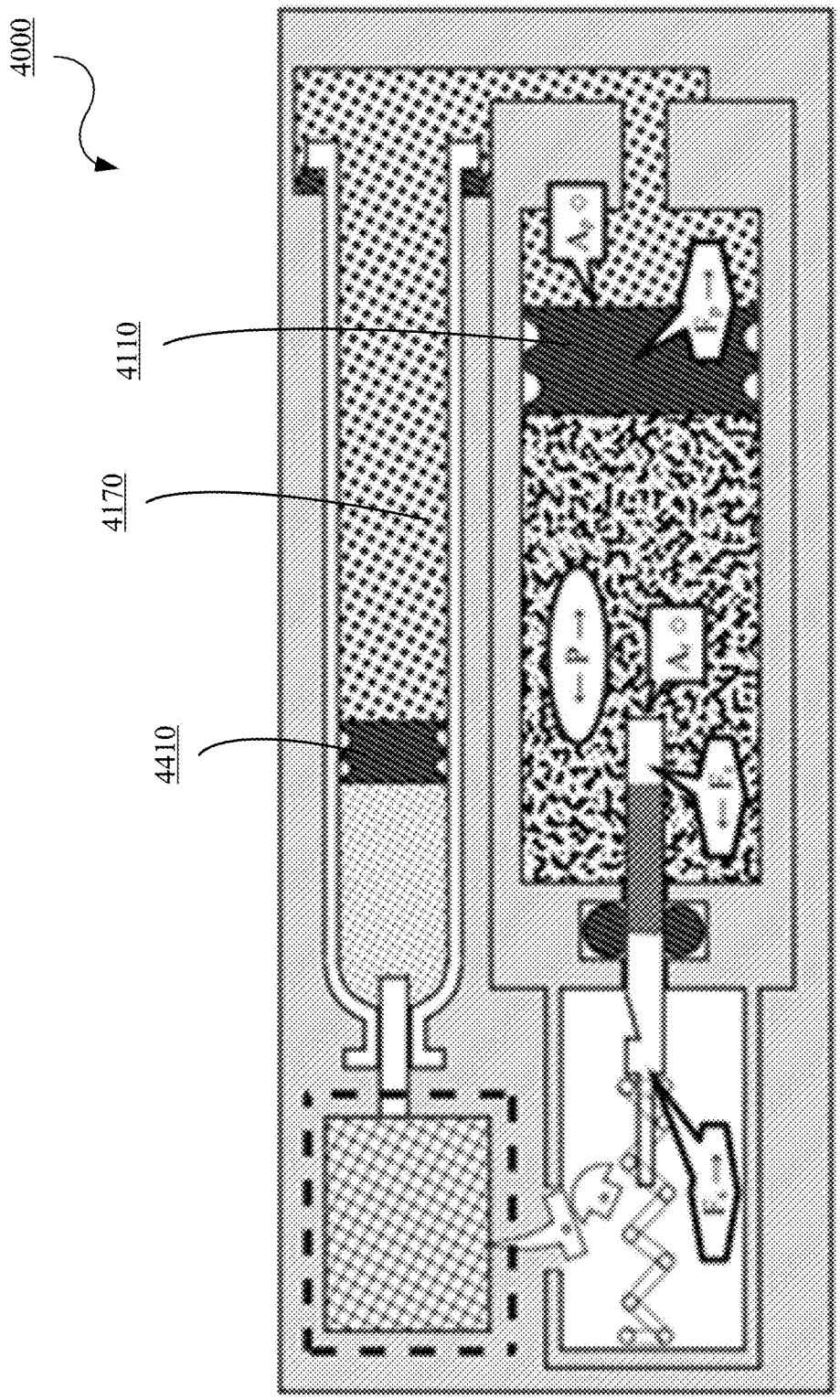
FIG. 4C is a block diagram of an example single use large volume injector in a later transactional state in accordance with implementations.
Figure 4D:
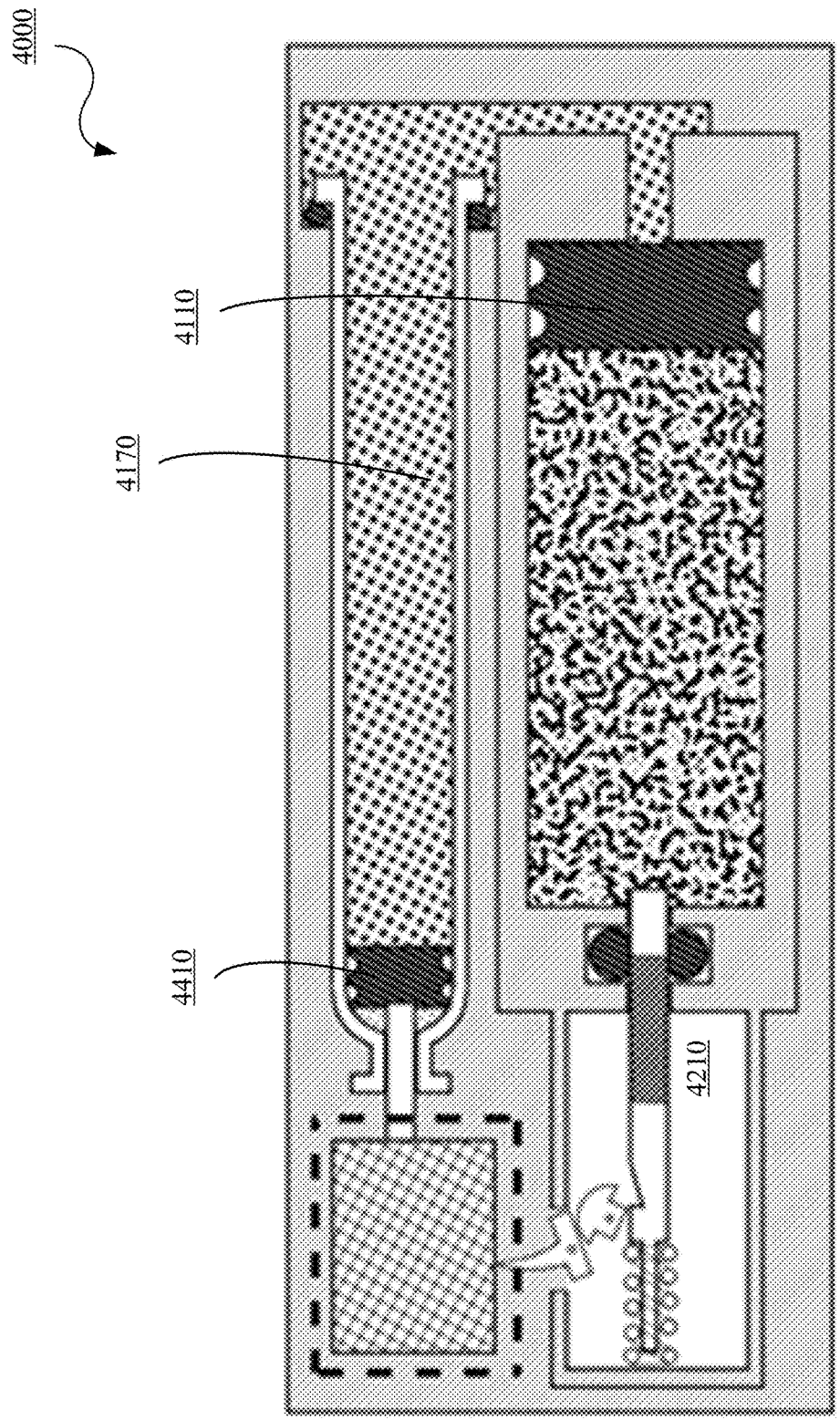
FIG. 4D is a block diagram of an example single use large volume injector in a retracted state in accordance with implementations.

FIG. 4A is a block diagram of an example single use large volume injector 4000 in an initial state accordance with implementations, FIG. 4B is a block diagram of the single use large volume injector 4000 in an early transactional state in accordance with implementations, FIG. 4C is a block diagram of the single use large volume injector 4000 in a later transactional state in accordance with implementations, and FIG. 4D is a block diagram of the single use large volume injector 4000 in a retracted state in accordance with implementations.

The single use large volume injector 4000 can include a container or housing 4100 (collectively "container") with a piston or plunger 4110 which moves within the container 4100. The container 4100 includes a rod opening 4120 and a gasket, o-ring, or similar structure 4130 on an inside surface of the container 4100 surrounding or circumscribing the rod opening 4120. The container 4100 includes a drive opening. The drive opening 4140 enables fluidic or hydraulic communication with an insertion device 4400. The container 4100 stores, holds, or contains a reagent 4160 between the rod opening 4120 and the piston 4110 and stores, holds, or contains a fluid or hydraulic medium 4170 between the piston 4110 and the insertion device 4300. In implementations, the reagent 4160 can be hydrogen peroxide ($H_2O_2$).

The single use large volume injector 4000 can include a control rod 4200 configured for insertion and retraction into the container 4100 through the rod opening 4120. The control rod 4200 includes a coated control rod section 4210. In implementations, a surface of the coated control rod section 4210 is coated with a catalyst. In implementations, the catalyst can be silver (Ag). In implementations, the surface of the coated control rod section 4210 is coated with a another or different reagent. The control rod 4200 includes a retention groove, indentation, lip, or the like (collectively "indentation") 4220.

As described herein, the control rod 4200 is initially positioned with the coated control rod section 4210 outside or external to the container 4100. The single use large volume injector 4000 includes a spring 4300 and a trigger mechanism 4310, which includes a trigger 4312 and a release and/or retraction mechanism 4314. The trigger mechanism 4310 holds the control rod 4200 in position pending activation or triggering of the single use large volume injector 4000 and when the control rod 4200 retracts from the container 4100 as described herein.

The insertion device 4400 includes a piston 4410, a barrel 4420, and a needle section 4430. The piston 4410 is in hydraulic contact with the piston 4110 via the hydraulic medium 4170. The piston 4410 is slidable in the barrel 4420. The barrel 4420, for example, stores a fluid such as a drug 4422. The needle section 4430 includes a needle 4432.

The single use large volume injector 4000 can include a user button 4500 connected to the trigger mechanism 4310 and the needle section 4430. The user button 4500 enables user initiated needle insertion and trigger activation of the single use large volume injector 4000. In implementations, the user button 4500 and the trigger mechanism 4310 can be an integrated mechanism.

The single use large volume injector 4000 is illustrative and may include additional, fewer or different parts, elements, and/or the like which may be similarly or differently architected without departing from the scope of the specification and claims herein. Moreover, the illustrated devices, parts, and/or elements may perform other functions without departing from the scope of the specification and claims herein.

Operationally, in an active state, the spring 4300 is in a compressed state and the trigger mechanism 4310 is engaged with the indentation 4220 to hold the control rod 4200 in position with the coated control rod section 4210 situated external or outside the container 4100. Upon a user pressing the user button 4500, the needle 4432 is inserted into the user to form a drug injection path and activates the single use large volume injector 4000 by causing the trigger 4312 and the release and/or retraction mechanism 4314 to disengage with the indentation 4220. This causes the control rod 4200 to push further into the container 4100 due to the spring 4300. The coated control rod section 4210 is brought into contact with the reagent 4160. The introduction of the coated control rod section 4210 with the reagent 4160 results in a chemical reaction. The catalyst coating causes decomposition of the reagent 4160. For example, hydrogen peroxide decomposes into oxygen, water, and heat when exposed to metallic silver. As gas and heat are released by the chemical reaction, pressure [P] rises internally acting on both the control rod 4200 and the piston 4110 until a dynamic equilibrium is reached where any further increase in pressure will cause the axial force on the control rod 4200 [$F_r$] to overcome the spring force [$F_s$] of the spring 4300 and retract the coated control rod section 4210 out of contact with the reagent 4160, halting the reaction. The maximum pressure generated by the reaction [$P_m$] is determined by the force of the spring 4300 and the cross sectional area of the end of the control rod 4200 [$A_r$] (since the remaining pressures on the control rod 4200 balance out). That is, $P_m = F_s/A_r$.

This pressure [$P_m$] acts to create a force on the piston 4110 [$F_p$] which is a function of the cross sectional area of the piston 4110 [$A_p$]. The acting force of the piston 4110 can be determined as a product of the force of the spring 4300 [$F_s$] and the ratio of the areas of the control rod 4200 [$A_r$] and the piston 4110 [$A_p$]. That is, $F_p = F_s(A_p/A_r)$. In addition, given the strong chemical reaction, the effective stroke length of the piston 3110 can be significantly longer than that of the spring 4300. In this fashion, the chemical reaction can be harnessed to do mechanical work substantially greater than the spring 4300 while being regulated by the spring 4300. The pressure [$P_m$] is applied by the piston 4110 onto the hydraulic medium 4170 which in turn applies the pressure [$P_m$] to the piston 4410. The piston 4410 slidably moves in the barrel 4420 to push or drive the drug 4422 through the needle section 4430 and the needle 4332 into the user regulated pressure which will result in a controlled rate of delivery.

Once the piston 4110 has reached the end of the travel, i.e., the end of the container 4100, the internal pressure will rise to fully overcome the spring force [$F_s$], fully retracting the control rod 4200 and halting the reaction. The release and/or retraction mechanism 4314 holds the control rod 4200 in place after retraction. The needle 4432 can also retract using a variety of mechanical techniques. For example, retraction of the needle 4432 can be triggered by the piston 4410 reaching the end of the barrel 4420 or when the control rod 4200 is completely retracted. For example, the user button 4500 can include a needle retracting mechanism driven by the piston 4410 or the control rod 4200 as described herein.

Figure 5:
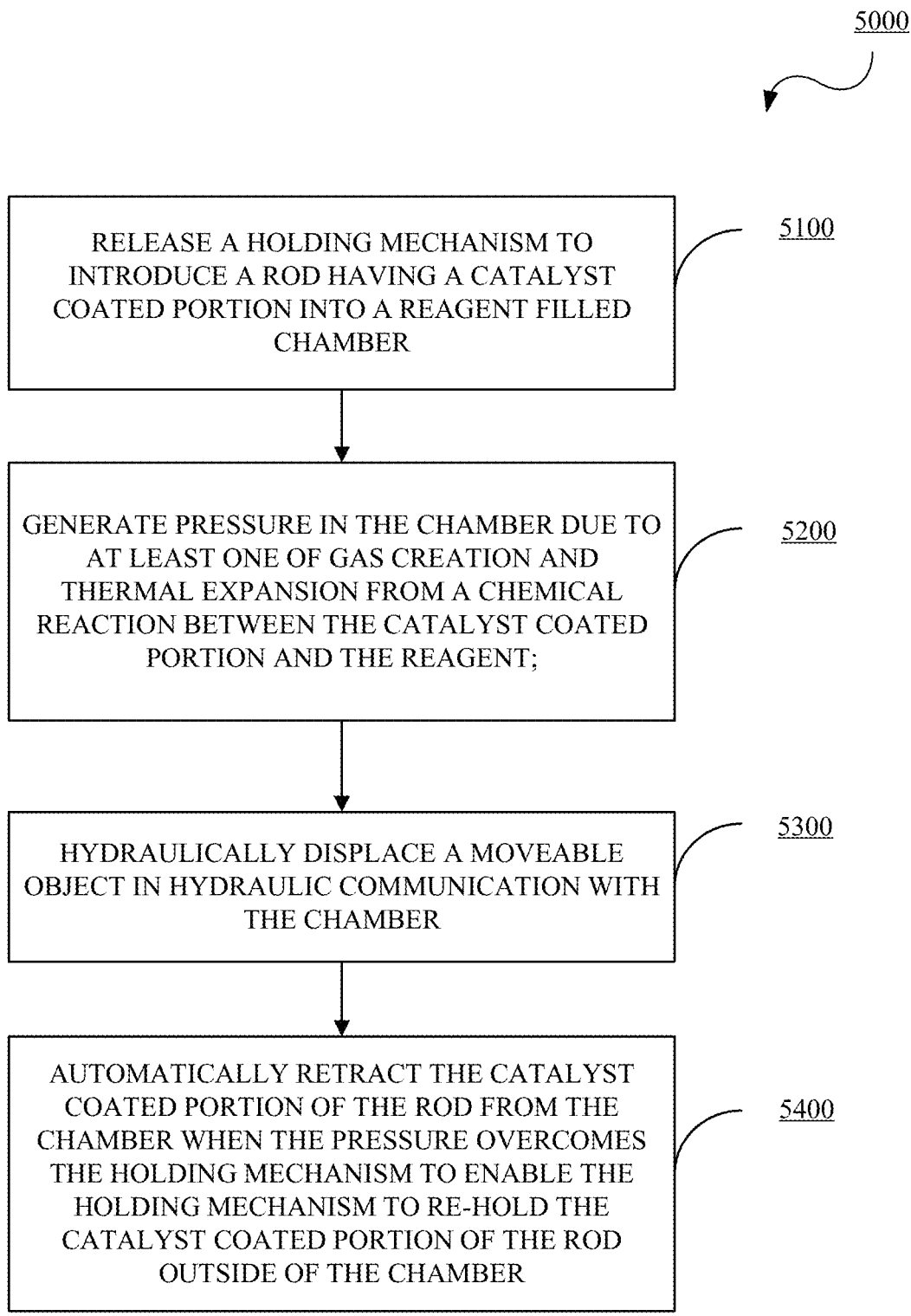
FIG. 5 is a flowchart of an example method for single use hydraulic drive in accordance with certain implementations.

FIG. 5 is a flowchart of an example technique or method 5000 for single use hydraulic drive in accordance with certain implementations. The method 5000 includes releasing 5100 a holding mechanism to introduce a rod having a catalyst coated portion into a reagent filled chamber; generating 5200 pressure in the chamber due to at least one of gas creation and thermal expansion from a chemical reaction between the catalyst coated portion and the reagent; hydraulically displacing 5300 a movable object in hydraulic communication with the chamber; and automatically retracting 5400 the catalyst coated portion of the rod from the chamber when the pressure overcomes the holding mechanism to enable the holding mechanism to re-hold the catalyst coated portion of the rod outside of the chamber. For example, the method 5000 may be implemented, as applicable and appropriate, by the single use large volume injector device 1000, the single use large volume injector 2000, the single use hydraulic drive device 3000, and the single use large volume injector 4000.

The method 5000 includes releasing 5100 a holding mechanism to introduce a rod having a catalyst coated portion into a reagent filled chamber. A device includes a holding mechanism, a rod having a catalyst coated portion, a chamber with a reagent, and a movable object. The holding mechanism maintains or holds the catalyst coated portion of the rod outside or external to the chamber in an initial or starting configuration. The device is activated by releasing the holding mechanism which in turn introduces the catalyst coated portion into the chamber. The releasing can be done using a trigger, a push button, or the like as described herein. The materials used for the reagent, the rod, and the reagent are as described herein. The movable or compressible object can be as described herein.

The method 5000 includes generating 5200 pressure in the chamber due to at least one of gas creation and thermal expansion from a chemical reaction between the catalyst coated portion and the reagent. Introduction of the catalyst coated portion into the chamber with the reagent causes a chemical reaction with generates pressure from gas creation and thermal expansion of the reagent.

The method 5000 includes hydraulically displacing 5300 a movable object in hydraulic communication with the chamber. The pressure eventually causes hydraulic displacement of the movable object.

The method 5000 includes automatically retracting 5400 the catalyst coated portion of the rod from the chamber when the pressure overcomes the holding mechanism to enable the holding mechanism to re-hold the catalyst coated portion of the rod outside of the chamber. At a defined range of time, the pressure reaches an equilibrium, overcomes a force of the holding mechanism, and retraction of the catalyst coated portion from the chamber occurs. That is, the pressure generation is self-regulating and enables a controlled rate of hydraulic displacement with respect to the movable object.

In general, a single use large volume injector device including a chamber configured to hold a reagent, a control rod configured for insertion and retraction into the chamber, the control rod including a catalyst coated portion, a holding mechanism configured to maintain the catalyst coated portion external to the chamber, and a syringe in hydraulic communication with the chamber, the syringe configured to hold a defined volume of an injectable fluid which is separated from the reagent by a movable barrier in the syringe. The self-regulating pressure in the chamber enables a controlled rate of injection of the injectable fluid by introduction of the catalyst coated portion into the chamber when the holding mechanism is released, generation of pressure in the chamber due to at least one of gas creation and thermal expansion from a chemical reaction between the catalyst coated portion and the reagent, hydraulic displacement of the movable barrier to inject the injectable fluid at the controlled rate, and retraction of the catalyst coated portion from the chamber when the pressure overcomes the holding mechanism to enable the holding mechanism to hold the catalyst coated portion outside of the chamber.

In implementations, the defined volume is at least 3 millimeters of a drug having up to 50 centipoise (CP) and the controlled rate is in the range of 5 seconds to 10 minutes. In implementations, the chamber includes a rod opening configured for insertion and retraction of the control rod, the rod opening circumscribed by a gasket on an internal surface of the chamber. In implementations, the chamber includes a drive opening configured for placement of the syringe, the drive opening circumscribed by a gasket on another internal surface of the chamber. In implementations, the single use large volume injector device further including a triggering mechanism configured to release the holding mechanism, a needle mechanism configured to insert a needle into a subject to establish an injection pathway, and an activation mechanism configured for trigger mechanism activation and needle insertion. In implementations, the chamber includes a drive opening configured for movable placement of the syringe, the drive opening circumscribed by a gasket on another internal surface of the chamber. In implementations, the holding mechanism and the rod opening are in a stacked configuration with respect to the drive opening and the syringe. In implementations, the chamber further including a movable barrier and a hydraulic fluid, wherein the movable barrier and the hydraulic fluid are in hydraulic communication with the syringe. In implementations, the holding mechanism and the rod opening are in a folded configuration with respect to the syringe.

In general, a single use hydraulic drive device including a housing configured to hold a first chemical material and a movable barrier, an insertion structure configured for movable placement into the housing, the insertion structure including a section coated with a second chemical material, and an activation mechanism configured to hold the section outside the housing. The self-regulating pressure in the housing enables a controlled rate of hydraulic displacement of the movable barrier by release of the section into the housing by activation of the activation mechanism, pressure generation in the housing due to gas creation and thermal expansion from chemical reactions between the first chemical material and the second chemical material, hydraulic displacement of the movable barrier in the housing at the controlled rate, and retraction of the catalyst coated portion from the chamber when the pressure overcomes the holding mechanism to enable the holding mechanism to hold the catalyst coated portion outside of the chamber.

In implementations, the housing includes an opening configured for movable placement of the insertion structure, the opening circumscribed by an o-ring on an internal side of the housing. In implementations, the activation mechanism further including a release and retraction device configured to engage the insertion structure and a trigger configured to release the release and retraction device. In implementations, the housing includes another opening configured for hydraulic communication with a movable object.

In general, a method for single use hydraulic drive including releasing a holding device to move a catalyst coated portion of a rod into a reagent filled chamber, generating pressure in the chamber due to at least one of gas creation and thermal expansion from a chemical reaction between the catalyst coated portion and the reagent, hydraulically displacing a movable object in hydraulic communication with the chamber, and stopping further chemical reaction when the pressure exceeds a holding device force threshold to enable the holding device to re-hold a retracted catalyst coated portion of the rod outside of the chamber. The self-regulating pressure in the chamber enables a controlled rate of hydraulic displacement of the movable object.

In implementations, the method further including generating pressure in the chamber due to a combination of the gas creation and the thermal expansion from the chemical reaction between the catalyst coated portion and the reagent. In implementations, the method further including automatically retracting the catalyst coated portion of the rod from the chamber when the pressure exceeds the holding device force threshold. the method further including the movable object is a piston in a syringe and the method further including delivering a defined volume of a drug via the syringe. In implementations, the defined volume is at least 3 millimeters of the drug having up to 50 centipoise (CP) and the controlled rate is in the range of 5 seconds to 10 minutes. In implementations, the method further including configuring the syringe in a stacked configuration with the single use hydraulic drive device. In implementations, the method further including configuring the syringe in a folded configuration with the single use hydraulic drive device.

The construction and arrangement of the methods as shown in the various exemplary embodiments are illustrative only. Although only a few embodiments have been described in detail in this disclosure, many modifications are possible (e.g., variations in sizes, dimensions, structures, shapes and proportions of the various elements, values of parameters, mounting arrangements, use of materials and components, colors, orientations, etc.). For example, the position of elements may be reversed or otherwise varied and the nature or number of discrete elements or positions may be altered or varied. Accordingly, all such modifications are intended to be included within the scope of the present disclosure. The order or sequence of any process or method steps may be varied or re-sequenced according to alternative embodiments. Other substitutions, modifications, changes, and omissions may be made in the design, operating conditions and arrangement of the exemplary embodiments without departing from the scope of the present disclosure.

Although the figures may show a specific order of method steps, the order of the steps may differ from what is depicted. Also two or more steps may be performed concurrently or with partial concurrence. Such variation will depend on the software and hardware systems chosen and on designer choice. All such variations are within the scope of the disclosure. Likewise, software implementations could be accomplished with standard programming techniques with rule-based logic and other logic to accomplish the various connection steps, processing steps, comparison steps, and decision steps.

While the disclosure has been described in connection with certain embodiments, it is to be understood that the disclosure is not to be limited to the disclosed embodiments but, on the contrary, is intended to cover various modifications and equivalent arrangements included within the scope of the appended claims, which scope is to be accorded the broadest interpretation so as to encompass all such modifications and equivalent structures as is permitted under the law.

What is claimed is:

1. A single use large volume injector device comprising:
   a chamber configured to hold a reagent;
   a control rod configured for insertion and retraction into the chamber, the control rod including a catalyst coated portion;
   a holding mechanism configured to maintain the catalyst coated portion external to the chamber; and
   a syringe in hydraulic communication with the chamber, the syringe configured to hold a defined volume of an injectable fluid which is separated from the reagent by a moveable barrier in the syringe,
   wherein a self-regulating pressure in the chamber enables a controlled rate of injection of the injectable fluid by:
      introduction of the catalyst coated portion into the chamber when the holding mechanism is released;
      generation of pressure in the chamber due to at least one of gas creation and thermal expansion from a chemical reaction between the catalyst coated portion and the reagent;
      hydraulic displacement of the moveable barrier to inject the injectable fluid at the controlled rate; and
      retraction of the catalyst coated portion from the chamber when the pressure overcomes the holding mechanism to enable the holding mechanism to hold the catalyst coated portion outside of the chamber.

2. The single use large volume injector device of claim 1, wherein the defined volume is at least 3 millimeters of a drug having up to 50 centipoise (CP) and the controlled rate is in the range of 5 seconds to 10 minutes.

3. The single use large volume injector device of claim 1, wherein the chamber includes a rod opening configured for insertion and retraction of the control rod, the rod opening circumscribed by a gasket on an internal surface of the chamber.

4. The single use large volume injector device of claim 3, wherein the chamber includes a drive opening configured for placement of the syringe, the drive opening circumscribed by a gasket on another internal surface of the chamber.

5. The single use large volume injector device of claim 4, further comprising:
   a triggering mechanism configured to release the holding mechanism;
   a needle mechanism configured to insert a needle into a subject to establish an injection pathway; and
   an activation mechanism configured for trigger mechanism activation and needle insertion.

6. The single use large volume injector device of claim 3, wherein the chamber includes a drive opening configured for moveable placement of the syringe, the drive opening circumscribed by a gasket on another internal surface of the chamber.

7. The single use large volume injector device of claim 3, wherein the holding mechanism and the rod opening are in a stacked configuration with respect to the drive opening and the syringe.

8. The single use large volume injector device of claim 3, the chamber further comprising a moveable barrier and a hydraulic fluid, wherein the moveable barrier and the hydraulic fluid are in hydraulic communication with the syringe.

9. The single use large volume injector device of claim 8, wherein the holding mechanism and the rod opening are in a folded configuration with respect to the syringe.

10. A single use hydraulic drive device comprising:
    a housing configured to hold a first chemical material and a moveable barrier;
    an insertion structure configured for moveable placement into the housing, the insertion structure including a section coated with a second chemical material; and
    an activation mechanism configured to hold the section coated with a second chemical material outside the housing,
    wherein a self-regulating pressure in the housing enables a controlled rate of hydraulic displacement of the moveable barrier by:
       release of the section coated with a second chemical material into the housing by activation of the activation mechanism;
       pressure generation in the housing due to gas creation and thermal expansion from chemical reactions between the first chemical material and the second chemical material;

hydraulic displacement of the moveable barrier in the housing at the controlled rate; and retraction of the section coated with a second chemical material from the chamber when the pressure overcomes the holding mechanism to enable the holding mechanism to hold the section coated with a second chemical material outside of the chamber.

11. The single use hydraulic drive device of claim 10, wherein the housing includes an opening configured for moveable placement of the insertion structure, the opening circumscribed by an o-ring on an internal side of the housing.

12. The single use hydraulic drive device of claim 11, the activation mechanism further comprising:
   a release and retraction device configured to engage the insertion structure; and
   a trigger configured to release the release and retraction device.

13. The single use hydraulic drive device of claim 12, wherein the housing includes another opening configured for hydraulic communication with a moveable object.

14. A method for single use hydraulic drive, the method comprising:
   releasing a holding device to move a catalyst coated portion of a rod into a reagent filled chamber;
   generating pressure in the chamber due to at least one of gas creation and thermal expansion from a chemical reaction between the catalyst coated portion and the reagent;
   hydraulically displacing a moveable object in hydraulic communication with the chamber; and
   stopping further chemical reaction when the pressure exceeds a holding device force threshold to enable the holding device to re-hold a retracted catalyst coated portion of the rod outside of the chamber,
   wherein self-regulating pressure in the chamber enables a controlled rate of hydraulic displacement of the moveable object.

15. The method of claim 14, further comprising:
   generating pressure in the chamber due to a combination of the gas creation and the thermal expansion from the chemical reaction between the catalyst coated portion and the reagent.

16. The method of claim 15, further comprising:
   automatically retracting the catalyst coated portion of the rod from the chamber when the pressure exceeds the holding device force threshold.

17. The method of claim 16, wherein the moveable object is a piston in a syringe and the method further comprising:
   delivering a defined volume of a drug via the syringe.

18. The method of claim 17, wherein the defined volume is at least 3 millimeters of the drug having up to 50 centipoise (CP) and the controlled rate is in the range of 5 seconds to 10 minutes.

19. The method of claim 18, the method further comprising:
   configuring the syringe in a stacked configuration with the single use hydraulic drive device.

20. The method of claim 18, the method further comprising:
   configuring the syringe in a folded configuration with the single use hydraulic drive device.

* * * * *